United States Patent
Bae et al.

(10) Patent No.: US 8,729,141 B2
(45) Date of Patent: May 20, 2014

(54) METHOD FOR METHANOL SYNTHESIS USING SYNTHESIS GAS GENERATED BY COMBINED REFORMING OF NATURAL GAS WITH CARBON DIOXIDE

(75) Inventors: Jong Wook Bae, Daejeon (KR); Jong Hyeok Oh, Daejeon (KR); Ki Won Jun, Daejeon (KR); Yun Jo Lee, Daejeon (KR); Jun-ho Ko, Ulsan (KR); Seok-Lyong Song, Ulsan (KR); Keh-Sik Min, Seoul (KR)

(73) Assignees: Hyundai Heavy Industries Co., Ltd., Ulsan (KR); Korea Research Institute of Chemical Technology, Daejeon (KR)

(*) Notice: Subject to any disclaimer, the term of this patent is extended or adjusted under 35 U.S.C. 154(b) by 370 days.

(21) Appl. No.: 13/132,471

(22) PCT Filed: Sep. 14, 2009

(86) PCT No.: PCT/KR2009/005215
§ 371 (c)(1),
(2), (4) Date: Jun. 2, 2011

(87) PCT Pub. No.: WO2010/067945
PCT Pub. Date: Jun. 17, 2010

(65) Prior Publication Data
US 2011/0237689 A1    Sep. 29, 2011

(30) Foreign Application Priority Data
Dec. 8, 2008 (KR) .................. 10-2008-0123865

(51) Int. Cl.
*C07C 27/00* (2006.01)

(52) U.S. Cl.
USPC .......................... 518/704; 518/702

(58) Field of Classification Search
CPC ................................... C07C 29/1518
USPC ................................ 518/702, 704
See application file for complete search history.

(56) References Cited

U.S. PATENT DOCUMENTS

| | | | |
|---|---|---|---|
| 6,100,303 A | 8/2000 | Hirotani et al. | |
| 6,218,439 B1 | 4/2001 | Kobayashi et al. | |
| 7,067,558 B2 | 6/2006 | Grobys et al. | |
| 2006/0287405 A1 | 12/2006 | Baek et al. | |

FOREIGN PATENT DOCUMENTS

| | | | |
|---|---|---|---|
| CN | 1144214 A | | 3/1997 |
| CN | 1891337 A | | 1/2007 |
| GB | 1159035 A | | 7/1969 |
| JP | 58-114730 A | | 7/1983 |
| KR | 10-0482646 | * | 4/2005 |
| KR | 10-0482646 B | | 4/2005 |
| KR | 10-2005-0051820 A | | 6/2005 |
| KR | 10-2006-0132293 A | | 12/2006 |
| KR | 10-2007-0043201 A | | 4/2007 |
| KR | 10-0732784 B | | 6/2007 |
| KR | 10-2010-0014012 A | | 2/2010 |

OTHER PUBLICATIONS

Shishido et al. (Catalysis Letters, vol. 73, No. 1, Apr. 2001, pp. 21-26).*
Hengyong Xu et al., "A study of the reforming of natural gas with steam, oxygen and carbon dioxide to produce syngas for methanol feedstock", Journal of Molecular Catalysis A: Chemical 147, 1999, pp. 41-16.
Aisling M. O'Connor et al., "The effect of $O_2$ addition on the carbon dioxide reforming of methane over $Pt/ZrO_2$ catalysts", Catalysis Today 46, 1998, pp. 203-210.
F. Frusteri et al., "Potassium-enhanced stability of Ni/MgO catalysis in the dry-reforming of methane", Catalysis Communications 2, 2001, pp. 49-56.
Deng Jingfa et al., "A novel process for preparation of $Cu/Zno/Al_2O_3$ ultrafine catalyst for methanol synthesis from $CO_2+H_2$: comparison of various preparation methods", Applied Catalysis A: General 139, 1996, pp. 75-85.

* cited by examiner

Primary Examiner — Rosalynd Keys
(74) Attorney, Agent, or Firm — Dickstein Shapiro LLP (57) ABSTRACT

Disclosed is a method for methanol synthesis using synthesis gas obtained from reforming of natural gas with carbon dioxide. First, synthesis gas is obtained from steam carbon dioxide reforming of methane, in which steam reforming of natural gas is carried out simultaneously with carbon dioxide reforming of methane, by using a catalyst (Ni/Ce/MgAlO$_x$, or Ni/Ce—Zr/MgAlO$_x$) and processing condition capable of maintaining a predetermined ratio of carbon monoxide, carbon dioxide, and hydrogen [$H_2/(2CO+3CO_2)$=0.85-1.15]. Next, methanol synthesis is carried out by using the obtained synthesis gas and a catalyst system suitable for methanol synthesis with minimum byproduct formation (a catalyst system including a Cu—Zn—Al oxide containing CuO, ZnO, and Al$_2$O$_3$ at a predetermined ratio in combination with a cerium-zirconium oxide obtained by a sol-gel process). In addition, unreacted synthesis gas remaining after the operation of methanol synthesis is recycled efficiently to improve the carbon availability (methane and $CO_2$ availability) and energy efficiency in the overall process.

6 Claims, 2 Drawing Sheets

(a) SCRM (STEAM CARBON DIOXIDE REFORMING OF METHANE)
= (SRM-STEAM REFORMING OF METHANE + CDR-CARBON DIOXIDE REFORMING)

(b) RR = RECYCLED RATIO (RECYCLED FLOW RATE/TOTAL FLOW RATE OF UNREACTED SYNTHESIS GAS)

Figure 3

METHOD FOR METHANOL SYNTHESIS USING SYNTHESIS GAS GENERATED BY COMBINED REFORMING OF NATURAL GAS WITH CARBON DIOXIDE

TECHNICAL FIELD

The present disclosure relates to a method for methanol synthesis using synthesis gas obtained from combined reforming of natural gas with carbon dioxide.

BACKGROUND ART

In 2005, as a measure to deal with global warming, the Kyoto protocol regarding reduction of carbon dioxide emission is enacted. Accordingly, there is an imminent need for providing methods for efficient use of carbon dioxide. In addition, as Clean Development Mechanism (CDM) industries are developed actively, particularly in advanced countries, carbon emission trading may be allowed according to the reduction of carbon dioxide. Therefore, it is expected that a success in development of efficient carbon dioxide utilization technologies has a great ripple effect in terms of economy. As processes for converting carbon dioxide, there have been suggested processes for preparing synthesis gas from combined reforming of natural gas, carbon dioxide and steam, and then producing useful chemical materials and transportation fuel from synthesis gas. Particularly, a process for synthesizing methanol, one of the most important chemical materials, or a process for preparing synthetic oil via Fischer-Tropsch synthesis by using synthesis gas obtained from the combined reforming, is getting important because it is regarded as an efficient way for utilization of carbon dioxide.

Processes for preparing synthesis gas from natural gas may be classified broadly into steam reforming of methane (SRM), partial oxidation of methane (POM) with oxygen, and carbon dioxide reforming of methane (CDR). The ratio of hydrogen to carbon monoxide ($H_2/CO$) is varied depending on the reforming process and should be adjusted to the optimal condition required for the subsequent process. In the case of a highly endothermic SRM process, it is possible to obtain a ratio of $H_2/CO$ of 3 or higher. Thus, the process is suitable for hydrogen production and ammonia preparation. In the case of POM, a ratio of $H_2/CO$ of about 2 is obtained. Thus, it is known that POM is suitable for methanol synthesis reaction and hydrocarbon formation through Fischer-Tropsch synthesis. However, POM is disadvantageous in that it requires a large-scale air-separation unit (ASU).

Hereinafter, the above-mentioned reforming processes are outlined with their advantages, disadvantages and the values of heat of reactions.

Steam Reforming of Methane (SRM)

$CH_4 + H_2O = 3H_2 + CO$  $\Delta H = 226$ kJ/mol

→ highly endothermic reaction, $H_2/CO>3$, excess steam is required.

Partial Oxidation of Methane (POM)

$CH_4 + 0.5O_2 = 2H_2 + CO$  $\Delta H = -44$ kJ/mol

→ mild exothermic reaction, $H_2/CO=2$, $O_2$ production process is required.

Carbon Dioxide Reforming of Methane (CDR)

$CH_4 + CO_2 = 2H_2 + 2CO$  $\Delta H = 261$ kJ/mol

→ highly endothermic reaction, $H_2/CO=1$, $CO_2$ addition is required.

In addition to the above reforming processes, there are known an auto-thermal reforming (ATR) process which is a combination of POM and SRM, a tri-reforming process which is a combination of POM, SRM and CDR, or the like in order to make an adequate $H_2/CO$ ratio as well as to increase energy and carbon efficiency. Further, it is possible to obtain synthesis gas having different $H_2/CO$ ratios depending on the type of reforming process and catalyst. Recently, many patent applications related to different methods using synthesis gas with such different $H_2/CO$ ratios (Korean Unexamined Patent Publication Nos. 2006-0132293 and 2005-0051820).

According to the present disclosure, a nickel-based reforming catalyst (Ni/Ce(Zr)MgAlO$_x$) is used to carry out steam carbon dioxide reforming of methane (SCRM), wherein the catalyst has high catalytic activity in the combined reforming in which SRM is carried out simultaneously with CDR, as disclosed in Korean Patent Application No. 2008-0075787 derived from our previous study. In this manner, synthesis gas is prepared to maintain carbon monoxide, carbon dioxide and hydrogen at a suitable composition [$H_2/(2CO+3CO_2)$] and a catalyst for combined reforming, which is suitable for methanol synthesis and Fischer-Tropsch synthesis using iron-based catalysts, is used. It is shown that the catalyst is inhibited not only from deactivation caused by carbon generation during the reaction but also from deactivation caused by nickel reoxidation due to water added during the reaction. Thus, the catalyst has excellent reactivity as compared to other known catalysts for combined reforming processes. In general, it is known that a ratio of $H_2/(2CO+3CO_2)$ in synthesis gas of about 1.05 is thermodynamically suitable for methanol synthesis. By adjusting the ratio to an adequate range, it is possible to increase methanol yield and carbon utilization efficiency. Therefore, it is required to add hydrogen in order to adjust the above ratio, or to modify processing parameters (temperature, pressure, etc.) in order to adjust the $CO_2$ conversion in CDR.

In the case of a currently available SRM process, a Ni/Al$_2$O$_3$ catalyst system is used at a reaction temperature of 750 to 850° C. under a molar ratio of steam/methane of 4-6:1. However, such a catalyst system is problematic in that it undergoes severe deactivation caused by carbon deposition. Therefore, many studies have been conducted about catalyst systems containing noble metals or transition metals and alkali metals as co-catalysts (*Journal of Molecular Catalysis A* 147 (1999) 41). In addition, in the case of a CDR process, more severe deactivation of catalysts occurs due to carbon deposition. Therefore, in order to inhibit such catalyst deactivation, many studies have been conducted about noble metal catalysts (Pt/ZrO$_2$) and Ni/MgO or Ni/MgAlO$_x$ catalyst systems, to which alkali metals are added as co-catalysts (*Catalysis Today* 46 (1998) 203, *Catalysis Communications* 2 (2001) 49, and Korean Unexamined Patent Publication No. 10-2007-0043201). In general, when using commercially available SRM catalysts directly to CDR and combined CDR and SRM processes, deactivation of catalysts caused by carbon deposition is accelerated.

It is generally known that methanol is produced from synthesis gas via the hydrogenation of carbon monoxide or carbon dioxide as depicted in the following reaction formulae:

$$CO + 2H_2 \leftrightarrow CH_3OH \quad \Delta H = -90.8 \text{ kJ/mol} \qquad (4)$$

$$CO_2 + 3H_2 \leftrightarrow CH_3OH + H_2O \quad \Delta H = -49.6 \text{ kJ/mol} \qquad (5)$$

$$CO + H_2O \leftrightarrow CO_2 + H_2 \quad \Delta H = -41.2 \text{ kJ/mol} \qquad (6)$$

Reaction formulae (4) and (5) are kinds of the exothermic volume-reducing reactions, and thus they prefer a low temperature and a high pressure thermodynamically. However, commercial production of methanol has been conducted at an adequate temperature to increase the reaction rate. In addition, the unreacted gases are recycled and used again in methanol synthesis in order to increase the availability of synthetic gas and to improve the conversion into methanol. However, water produced according to Reaction Formula (5) causes water gas shift reaction (WGS), such as one as shown in reaction formula (6), thereby forming an excessive amount of $CO_2$ as a byproduct. Therefore, when introducing a catalyst and process capable of improving the yield of methanol synthesis by adjusting such parameters adequately, it is possible to improve the carbon utilization and energy utilization efficiency of the overall process. In this context, many workers have participated in studies for improving the quality of catalysts for methanol synthesis, but complete understanding about the active site of a catalyst for methanol synthesis cannot be accomplished heretofore. However, it is known that oxidation state of Cu and redox conversion property of reduced Cu particles play an important role in determining the catalyst quality. It is also known that the activity of a Cu catalyst in a reaction of methanol synthesis is in proportion to the specific surface area of Cu of the metal components. For this reason, Cu is used frequently in combination with Zn to prepare the catalyst, and a molar ratio of Cu/Zn of 3/7 is known to provide the highest activity. However, it is known that when $CO_2$ is present or when the proportion of oxygen-containing materials that cover the $Cu^0$ surface increases, the catalyst activity is independent from the $Cu^0$ surface area. Particularly, Korean Patent Application No. 2008-0072286, derived from our previous study about methanol synthesis from synthesis gas, discloses a novel catalyst system, including a Cu—Zn—Al oxide containing CuO, ZnO and $Al_2O_3$ in a predetermined ratio, in combination with a cerium-zirconium oxide obtained by a sol-gel process. More particularly, the above patent application relates to a catalyst for synthesizing methanol from synthesis gas and a method for synthesizing the same, wherein the catalyst is capable of inhibiting formation of byproducts and improving selectivity toward methanol as compared to the other catalysts using Cu—Zn—Al alone, thereby improving carbon conversion efficiency and energy efficiency in methanol synthesis.

In addition to the above, according to the existing patent publications about methanol synthesis from synthesis gas, $CO_2$ is reused in a reformer to minimize emission of $CO_2$ produced during POM and a cryogenic separation method is employed in such a manner that $H_2$-rich gas is used for methanol synthesis or as fuel, while CO-rich gas is used in a process for acetic acid preparation, thereby improving the energy efficiency of the overall process (U.S. Pat. No. 7,067,558). Meanwhile, U.S. Pat. No. 6,100,303 discloses a process for improving energy efficiency and $CO_2$ availability, wherein two different types of reformers, i.e., a combustion type reformer and a heat exchanger type reformer, are used for steam reforming of natural gas, and purge gas in the unreacted gases is used as a raw material for reforming/methanol synthesis and as fuel of the reformers in order to reduce the cost required for constructing the processing system and to improve energy efficiency. However, the process of the U.S. Pat. No. 6,100,303 is different from the present disclosure in terms of the construction of the overall process and recycling process. Further, U.S. Pat. No. 6,218,439 discloses a method for utilization of $CO_2$ generated during the reaction based on steam reforming alone, wherein $CO_2$ emission is minimized by refeeding $CO_2$ into reforming or into methanol synthesis after the separation of products. However, the method of the U.S. Pat. No. 6,218,439 patent uses a catalyst different from the catalyst system disclosed herein and is differentiated from the present disclosure in terms of the construction of the overall process and recycling process.

DISCLOSURE

Technical Problem

Under these circumstances, we have focused on a method for improving carbon availability and energy efficiency in a process for methanol preparation using carbon dioxide. First, synthesis gas is obtained from steam carbon dioxide reforming of methane (SCRM), in which steam reforming of natural gas is carried out simultaneously with carbon dioxide reforming of methane, by using a catalyst (Ni/Ce/MgAlO$_x$ or Ni/Ce—Zr/MgAlO$_x$) and processing condition capable of maintaining a predetermined ratio of carbon monoxide, carbon dioxide and hydrogen [$H_2/(2CO+3CO_2)$=0.85–1.15]. Next, methanol is synthesized by using the obtained synthesis gas and a catalyst suitable for methanol synthesis with minimum byproduct formation (a catalyst system including a Cu—Zn—Al oxide containing CuO, ZnO and $Al_2O_3$ in a predetermined ratio, in combination with a cerium-zirconium oxide obtained by a sol-gel process). In addition, unreacted synthesis gas remaining after the operation of methanol synthesis is recycled efficiently to improve the carbon availability (methane and $CO_2$ availability) and energy efficiency in the overall process.

The present disclosure is directed to providing a method for methanol synthesis using synthesis gas obtained from combined reforming of natural gas with carbon dioxide.

Technical Solution

In one aspect, there is provided a method for methanol preparation from carbon dioxide, including:

preparing synthesis gas via combined reforming, in which steam reforming of natural gas is carried out simultaneously with carbon dioxide reforming of methane, in the presence of a catalyst of Ni/Ce/MgAlO$_x$ or Ni/Ce—Zr/MgAlO$_x$;

synthesizing methanol from the obtained synthesis gas in the presence of a catalyst of Cu—ZnO—Al$_2$O$_3$/CeZrOx; and separating the methanol product from unreacted synthesis gas and recycling the unreacted synthesis gas.

Advantageous Effects

The present disclosure provides, as a measure of economic utilization of carbon dioxide, an integrated method that includes carrying out combined reforming (carbon dioxide reforming of methane carried out simultaneously with steam reforming) to produce synthesis gas suitable for methanol synthesis by maintaining a predetermined ratio of carbon monoxide, carbon dioxide and hydrogen. Herein, a catalyst for combined reforming according to our previous study (Korean Patent Application No. 2008-0075787) and a catalyst for methanol synthesis according to our previous study (Korean Patent Application No. 2008-0072286) are used, and unreacted synthesis gas remaining after the methanol synthesis is recycled at an adequate recycle ratio. In this manner, it is possible to maximize carbon availability (methane and $CO_2$ availability) and energy efficiency in the overall process. It is expected that such chemical utilization of carbon dioxide reduces carbon dioxide emission and provides a substitute for methanol imports.

MODE FOR INVENTION

As mentioned above, one aspect of the present disclosure provides a method for preparing methanol from carbon dioxide, including:

preparing synthesis gas via combined reforming, in which steam reforming of natural gas is carried out simultaneously with carbon dioxide reforming of methane, in the presence of a catalyst of $Ni/Ce/MgAlO_x$ or $Ni/Ce$—$Zr/MgAlO_x$;

synthesizing methanol from the obtained synthesis gas in the presence of a catalyst of $Cu$—$ZnO$—$Al_2O_3/CeZrOx$; and separating the methanol product from unreacted synthesis gas and recycling the unreacted synthesis gas.

Hereinafter, the method will be explained in more detail.

First, the method disclosed herein includes preparing synthesis gas according to our previous study (Korean Patent Application No. 2008-0075787) from steam carbon dioxide reforming of methane (SCRM), in which steam reforming of natural gas is carried out simultaneously with carbon dioxide reforming of methane, while maintaining a predetermined ratio of carbon dioxide, carbon dioxide and hydrogen [$H_2/(2CO+3CO_2)$=0.85–1.15]. In addition, the method disclosed herein includes synthesizing methanol by using the obtained synthesis gas and a catalyst capable of minimizing byproduct formation according to our previous study (Korean Patent Application No. 2008-0072286). Further, unreacted synthesis gas remaining after the operation of methanol synthesis is recycled with an adequate ratio to improve the carbon availability (methane and $CO_2$ availability). In this manner, it is possible to prepare methanol from carbon dioxide with improved methanol yield.

Generally, in SRM and CDR processes, equilibrium conversion is determined by the ratio of reactants, $CH_4/CO_2/$steam, reaction pressure and reaction temperature. CDR equilibrium conversion decreases and carbon deposition rate increases, as the reaction pressure increases. However, in an industrial plant, reactors are downsized to reduce the initial cost requirement and reforming is carried out usually at a reaction pressure of 1.0 MPa or higher in order to reduce the cost required for the subsequent separation operation. In such combined reforming processes, $CO_2$ conversion decreases as the reaction pressure and steam amount in a feed composition increase. Thus, it is advisable to minimize the use of steam. However, this adversely affects the life of a catalyst due to carbon deposition, and thus there is a need for developing a catalyst inhibited from deactivation under the above-mentioned conditions. More particularly, as shown in the following Tables 1, 2 and 3, in which equilibrium conversions of combined reforming calculated thermodynamically are described, $CO_2$ conversion in the combined reforming decreases as the reaction pressure and steam content in the feed composition increase, while $CO_2$ conversion increases as the reaction temperature increases. In addition, equilibrium conversion of combined reforming and $H_2/(2CO+3CO_2)$ ratio are varied with the feed composition and reaction temperature. Therefore, in order to allow synthesis gas to maintain a predetermined ratio ($H_2/(2CO+3CO_2)$=0.85–1.15), it is necessary to adjust the molar ratio of reactants (methane, carbon dioxide and steam), reaction pressure and reaction temperature, and it is important to employ a suitable catalyst.

TABLE 1

Variations in Equilibrium Conversion Depending on Feed Composition and Temperature/Pressure (Feed Composition: $CH_4/H_2O/CO_2$ = 1/1.5/x (Molar Ratio) at 900° C., 0.5-1.0 MPa)

| | P = 0.5 MPa | | | P = 1.0 MPa | |
|---|---|---|---|---|---|
| $CO_2$ Ratio | $CH_4$ Conversion (%) | $CO_2$ Conversion (%) | $CO_2$ Ratio | $CH_4$ Conversion (%) | $CO_2$ Conversion (%) |
| 0.3 | 96.98 | 36.67 | 0.3 | 90.87 | 32.33 |
| 0.4 | 97.14 | 40.00 | 0.4 | 91.75 | 40.50 |
| 0.5 | 97.35 | 43.75 | 0.5 | 92.54 | 44.80 |
| 0.6 | 97.67 | 47.40 | 0.6 | 93.25 | 47.33 |
| 0.7 | 98.17 | 49.50 | 0.7 | 93.88 | 48.71 |
| 0.8 | 98.37 | 50.57 | 0.8 | 94.45 | 49.63 |
| 0.9 | 98.54 | 51.25 | 0.9 | 94.96 | 50.11 |
| 1.0 | 98.69 | 51.44 | 1.0 | 95.42 | 50.30 |

TABLE 2

Variations in Equilibrium Conversion Depending on Feed Composition and Temperature/Pressure (Feed Composition: $CH_4/H_2O/CO_2$ = 1/2.0/x (Molar Ratio) at 900° C., 0.5-1.0 MPa)

| | P = 0.5 MPa | | | P = 1.0 MPa | |
|---|---|---|---|---|---|
| $CO_2$ Ratio | $CH_4$ Conversion (%) | $CO_2$ Conversion (%) | $CO_2$ Ratio | $CH_4$ Conversion (%) | $CO_2$ Conversion (%) |
| 0.3 | 98.39 | 8.33 | 0.3 | 94.53 | 6.00 |
| 0.4 | 98.54 | 21.25 | 0.4 | 94.94 | 19.50 |
| 0.5 | 98.66 | 28.60 | 0.5 | 95.33 | 27.20 |
| 0.6 | 98.78 | 33.33 | 0.6 | 95.69 | 32.17 |
| 0.7 | 98.89 | 36.29 | 0.7 | 96.02 | 35.29 |
| 0.8 | 98.98 | 38.38 | 0.8 | 96.33 | 37.50 |
| 0.9 | 99.07 | 39.78 | 0.9 | 96.61 | 38.89 |
| 1.0 | 99.14 | 40.70 | 1.0 | 96.87 | 40.00 |

TABLE 3

Variations in Equilibrium Conversion and $H_2/(2CO + 3CO_2)$ Ratio (0.1 MPa) Depending on Feed Composition/Reaction Temperature

| Reactant Composition $CH_4:CO_2:H_2O$ (molar ratio) | Conversion (%) | 700° C. | 800° C. | 900° C. | 1000° C. |
|---|---|---|---|---|---|
| 1:0.4:1 | $CH_4$ | 86 | 98 | 100 | 100 |
| | $CO_2$ | 45 | 66 | 73 | 78 |
| | $H_2/CO$ | 2.31 | 2.16 | 2.09 | 2.05 |
| | $H_2/(2CO + 3CO_2)$ | 0.88 | 0.92 | 0.93 | 0.93 |
| 1:0.86:2 | $CH_4$ | 74 | 98 | 100 | 100 |
| | $CO_2$ | 15 | 30 | 40 | 48 |
| | $H_2/CO$ | 2.34 | 2.20 | 1.99 | 1.85 |
| | $H_2/(2CO + 3CO_2)$ | 0.63 | 0.48 | 0.39 | 0.32 |
| 1:0.44:2 | $CH_4$ | 94 | 98 | 100 | 100 |
| | $CO_2$ | −12 | 10 | 25 | 36 |
| | $H_2/CO$ | 3.24 | 2.83 | 2.60 | 2.45 |
| | $H_2/(2CO + 3CO_2)$ | 0.88 | 0.90 | 0.90 | 0.90 |

As shown in Tables 1, 2 and 3, combined reforming may be operated under a pressure ranging from ambient pressure to 20 atm. However, in the case of low pressure, equilibrium conversion increases, while the reactor volume increases, resulting in an increase in initial cost. In addition, a high-pressure system is required additionally for the separation of the product, resulting in degradation of cost-efficiency. On the other hand, under an operating condition above 20 atm, deactivation of catalyst is accelerated and equilibrium conversion of methane and carbon dioxide decreases. Therefore, it is necessary to maintain an adequate operating condition. To maintain an optimized feed condition of $H_2/(2CO+3CO_2)$ molar ratio of 0.85 to 1.15, it is required for the reforming reactants to maintain a $CH_4/CO_2/H_2O$ molar ratio of 1/0.3–0.6/1.0–2.0. When the molar ratio of $H_2O$ based on methane is 1.0 or less, deactivation of catalyst caused by carbon deposition becomes severe. On the other hand, when the molar ratio exceeds 2.0, $CO_2$ conversion decreases and $CO_2$ availability also decreases, as demonstrated in Tables 1, 2 and 3.

Figure 1:
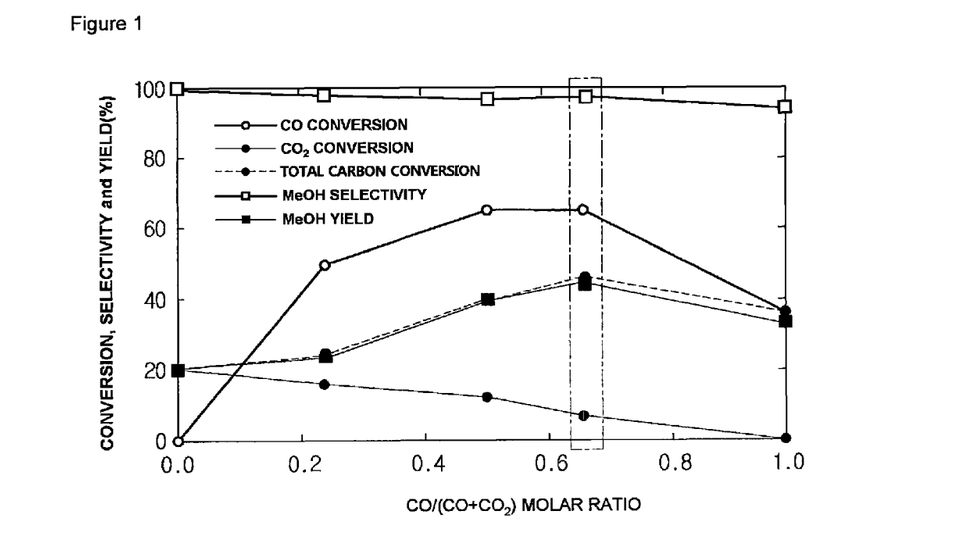
FIG. 1 is a graph showing methanol yield in a reaction of methanol synthesis as a function of CO/(CO+$CO_2$) ratio.

In general, as shown in FIG. 1, in a reaction for methanol synthesis, methanol yield is improved in the presence of synthesis gas containing a predetermined amount of $CO_2$ as compared to synthesis gas merely containing CO and $H_2$. It can be seen that methanol yield is maximized under a molar ratio of $CO/(CO+CO_2)$ of 0.6 to 0.8. Therefore, the SRM/CDR combined reforming suggested herein allows preparation of synthesis gas suitable for methanol synthesis by maintaining a predetermined ratio of carbon monoxide, carbon dioxide and hydrogen ($H_2/(2CO+3CO_2)=0.85-1.15$), making it possible to maximize methanol synthesis efficiency. In this manner, the method disclosed herein is very useful for processes for preparing methanol from carbon dioxide.

Figure 2:
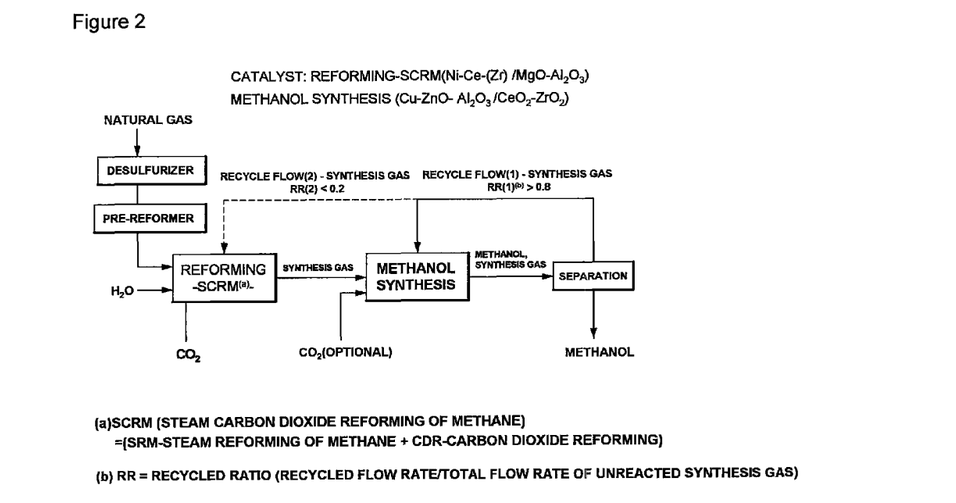
FIG. 2 is a schematic flow chart illustrating methanol synthesis using synthesis gas obtained from combined reforming of carbon dioxide, methane and water according to an embodiment of the method disclosed herein.

In addition, as shown in FIG. 2, the method disclosed herein includes an integrated process of three main unit operations, i.e., reforming, methanol synthesis and separation. First, combined reforming (steam carbon dioxide reforming of methane: SCRM) is carried out by using our previous study for combined reforming (Korean Patent Application No. 2008-0075787), wherein steam reforming of natural gas ($CH_4$) (SRM) is performed simultaneously with carbon dioxide reforming of methane (CDR). Herein, the resultant synthesis gas of carbon monoxide, carbon dioxide and hydrogen is allowed to maintain a predetermined molar ratio ($H_2/(2CO+3CO_2)=0.85-1.15$) so that it is suitable for methanol synthesis. In the subsequent methanol synthesis, a catalyst system for methanol synthesis capable of minimizing formation of byproducts according to our previous study (Korean Patent Application No. 2008-0072286) is used. The method disclosed herein is characterized by such an integrated process capable of maximizing carbon availability (methane and $CO_2$ availability) and energy efficiency. Before carrying out the combined reforming, sulfur compounds contained in natural gas is removed by pretreatment using generally known adsorptive desulfurization or hydrodesulfurization processes to inhibit deactivation of reforming catalyst. In addition, $C_2$-$C_4$ hydrocarbons in natural gas are preliminarily converted in a pre-reformer before they are fed into a combined reforming reactor at high temperature, so that catalyst deactivation caused by carbon production is inhibited in the subsequent operation. The combined reforming is carried out by performing steam reforming of natural gas simultaneously with carbon dioxide reforming of methane, thereby maximizing carbon dioxide availability. The combined reforming is carried out by using a catalyst obtained by supporting Ni as an active ingredient on $Ce/MgAlO_x$ or $Ce-Zr/MgAlO_x$ as a carrier in a weight ratio of 5 to 20 wt % based on the carrier, followed by calcination at 600 to 1,000° C., and having a specific surface area of 80 to 200 $m^2/g$ (Korean Patent Application No. 2008-0075787). In addition, the catalyst is reduced at a temperature of 700 to 1,000° C. before the reaction, and then the combined reforming is carried out at a temperature of 800 to 1,000° C. under a reaction pressure of 0.5 to 20 atm with a space velocity of 1,000 to 500,000 $h^{-1}$. Then, the resultant synthesis gas is used for the subsequent methanol synthesis while maintaining a predetermined molar ratio ($H_2/(2CO+3CO_2)=0.85-1.15$). In the operation of methanol synthesis, a catalyst system including a cerium-zirconium oxide obtained by a sol-gel process in combination with a Cu—Zn—Al oxide at a weight ratio of 0.1 to 10 based on the cerium-zirconium oxide according to our previous study (Korean Patent Application No. 2008-0072286) is used. Particularly, the cerium-zirconium oxide obtained by a sol-gel process has a Ce/Zr ratio of $0.02<Ce/Zr<0.5$ and a specific surface area of 100 to 300 $m^2/g$, and the finished catalyst for methanol synthesis, $Cu—Zn—Al/CeO_2—ZrO_2$ has a specific surface area of 50 to 250 $m^2/g$. The catalyst for methanol synthesis is reduced at a temperature ranging from 200 to 500° C. under hydrogen atmosphere, and then a reaction for methanol synthesis is carried out at a temperature of 200 to 400° C. under a pressure of 30 to 60 $kg/cm^2$ with a space velocity of 1,000 to 10,000 $h^{-1}$. The final product, methanol, and unreacted reactants are separated from each other by a separation process generally known to those skilled in the art, and the unreacted reactants are recycled to the reactors for combined reforming and methanol synthesis. In this connection, the recycle ratio (RR=recycle flow rate/total flow rate of unreacted reactants) is controlled adequately to maximize carbon availability and energy efficiency in the overall process. The recycle ratio (RR(2)) of unreacted reactants recycled to combined reforming and that (RR(1)) of unreacted reactants recycled to methanol synthesis are maintained below 20% and above 80%, respectively, based on the total recycle flow, so that reutilization of synthesis gas may be maximized in the reactor for methanol synthesis. In this manner, it is possible to improve energy efficiency and carbon availability in the overall process. For example, when the recycle ratio toward combined reforming is greater than 20%, high energy consumption is required to increase the temperature to a high temperature of 800° C. or higher before the combined reforming, or synthesis gas, CO or $H_2$, contained in the recycle flow in an excessive amount may function as a diluting gas, leading to degradation of energy efficiency. In addition, when the recycle ratio toward methanol synthesis is lower than 80%, the amount of reactants for methanol synthesis is decreased, resulting in a drop in methanol yield. Therefore, it is required to control the recycle ratio of unreacted reactants adequately, so that the ratio of $H_2/(2CO+3CO_2)$ is maintained at a range of 0.85 to 1.15 favorable to methanol synthesis even if $CO_2$ contained in the reactants is concentrated during the recycling. Such control of the recycle ratio increases carbon availability (one-pass conversion) in methanol synthesis, and thus maximizes energy efficiency and carbon availability.

Figure 3:
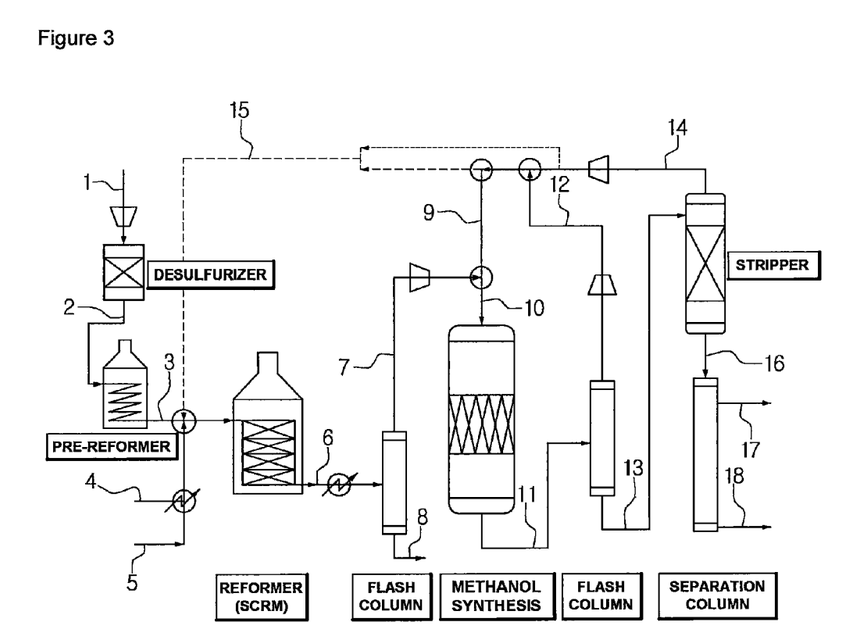
FIG. 3 is a schematic diagram of the method disclosed herein, including preparing synthesis gas via combined reforming, synthesizing methanol from the synthesis gas, and separating and purifying the product.

FIG. 3 is a schematic diagram of the method including combined reforming and methanol synthesis and providing maximized energy efficiency and carbon availability. The method broadly includes carrying out combined reforming, carrying out methanol synthesis, and carrying out separation and recycling. First, natural gas is passed into a desulfurizer by way of stream 1. The desulfurization process used herein is a generally known adsorption desulfurization or hydrodesulfurization process capable of removing sulfur components in natural gas. By doing so, it is possible to inhibit deactivation of reforming catalyst and to prevent corrosion inside of the reactor and conveying lines. Then, stream 2 free from sulfur components is passed through a pre-reformer, wherein $C_2$-$C_4$ hydrocarbons in natural gas are reformed first in order to inhibit deactivation of catalyst caused by carbon formation in a combined reforming reactor with high temperature. Thus, after such pretreatment, stream 3 essentially includes methane and reformed gas. Water (stream 4) as one of the reactants for combined reforming is subjected to heat exchange and supplied as a reactant in the form of highly pressurized steam. Carbon dioxide reactant, stream 5, is also subjected to heat exchange, combined with stream 3 and stream 4, and then is fed into the combined reforming reactor heated to 700° C. or higher. Herein, stream 15 composed of unreacted reactants and containing an excessive amount of $CO_2$ is combined with the above streams, while maintaining a recycle ratio (RR(2)) of 0.2 or less, and then supplied to the combined reforming reactor. After the combined reforming, the product, stream 6 is passed through a flash column, which is a gas-liquid separator, and unreacted water and other high-boiling point products passed through the flash column is discharged as stream 8, which, in turn, is purified to provide water capable of being reused as processing water. On the other hand, synthesis gas (stream 7) as a reactant for methanol synthesis is boosted to a high pressure of 30 atm or higher suitable for methanol synthesis, is subjected to heat exchange, and then is fed to a reactor for methanol synthesis. The reactants for methanol synthesis is further combined with stream 9 derived from recycling of unreacted synthesis gas after methanol synthesis and maintaining a recycle ratio of 0.8 or higher, is subjected to heat exchange, and then is fed to the reactor for methanol synthesis along stream 10. Then, stream 11 passed through methanol synthesis from synthesis gas is sent to a flash column (a gas-liquid separator) to perform gas-liquid separation. After the separation, stream 13 formed of the main product, methanol, and byproducts essentially including water and $CO_2$ dissolved in stream 13 are sent to the next separation unit. Unreacted synthesis gas is recycled as stream 12, which, in turn, is reutilized in the combined reforming reactor and reactor for methanol synthesis while maintaining an adequate recycle ratio. Stream 13 containing the main product is passed through a stripper first to separate $CO_2$ and is conveyed as stream 14, which, in turn, is combined with stream 12 to be recycled. Herein, stream 12 and stream 14 are boosted before they are recycled to methanol synthesis in order to compensate for a pressure drop occurring in the separation. As an alternative, stream 14 is fed merely into the combined reforming reactor so as to inhibit a drop in methanol yield caused by an increase in $CO_2$ concentration in the reactor for methanol synthesis. Finally, stream 16 passes from the stripper into a separation unit for purifying methanol, so that high-purity methanol is discharged as stream 17 and water and dissolved $CO_2$ are discharged as stream 18, which, in turn, is purified and recycled. Herein, stream 9 and stream 15 are maintained at a recycle ratio of 0.8 or higher and 0.2 or less, respectively, in order to maximize energy efficiency and carbon availability in the overall process for preparing methanol from carbon dioxide. The catalysts that may be used in the method including carrying out reforming, carrying out methanol synthesis and carrying out separation are based on our previous studies. First, a catalyst for combined reforming according to our previous study (Korean Patent Application No. 2008-0075787) is used in such a manner that the resultant synthesis gas has a predetermined molar ratio of carbon monoxide, carbon dioxide and hydrogen ($H_2/(2CO + 3CO_2)$=0.85-1.15). Next, a catalyst for methanol synthesis according to our previous study (Korean Patent Application No. 2008-0072286) is used to minimize formation of byproducts. In addition to the above, unreacted synthesis gas is recycled at an adequate recycle ratio to maximize carbon availability (methane and $CO_2$ availability) and energy efficiency.

The examples (and experiments) will now be described. The following examples (and experiments) are for illustrative purposes only and not intended to limit the scope of the present disclosure.

EXAMPLE 1

A catalyst for combined reforming is prepared according to our previous study (Korean Patent Application No. 2008-0075787).

First, PURAL MG30 (available from Sasol, specific surface area: at least 250 $m^2/g$), which is $MgAlO_x(30)$ with a hydrotalcite structure having an $MgO/Al_2O_3$ ratio of 3/7, is provided as a catalyst carrier for combined reforming. Next, the $MgAlO_x(30)$ carrier is impregnated with cerium acetate and zirconium acetate in such a manner that Zr/Ce ratio is 0.25 on the weight basis and Ce—Zr is carried on the $MgAlO_x$ (30) carrier at a ratio of 18 wt % based on the total weight of the carrier. At the same time, nickel nitrate hexahydrate ($Ni(NO_3)_2 \cdot 6H_2O$) as a nickel precursor is supported on the Ce—$Zr/MgAlO_x(30)$ carrier at a weight ratio of 15 wt % based on the total weight of the carrier. Then, the resultant product is agitated in a vacuum drier at 70° C. reactor, and is reduced under hydrogen atmosphere (10 vol % $H_2/N_2$) at 750° C. for 5 hours, and a combined reforming reaction is carried out. To the reforming reactor, reactants including $CH_4$, $CO_2$ and $H_2O$ at a fixed molar ratio of 1:0.4:1.5 ($CH_4$:$CO_2$:$H_2O$) are fed at a reaction temperature of 850° C. under a reaction pressure of 0.5 MPa with a space velocity of 1300 L/kg cat/h. The catalyst bed shows a distribution of reaction temperature ranging from 795° C. to 981° C.

Then, a catalyst for methanol synthesis is prepared according to our previous study (Korean Patent Application No. 2008-0072286).

A cerium-zirconium oxide as a carrier is provided by a sol-gel process.

First, 12.06 g of citric acid and 14.32 g of ethylene glycol are dissolved at 60° C. for 30 minutes under agitation. Next, 2.50 g of cerium nitrate hexahydrate ($Ce(NO_3)_2 6H_2O$) as a Ce precursor is dissolved in a minimum amount of water equal to or less than 30 mL so that it is dissolved completely therein, and then the resultant solution is added gradually to the preformed mixture of citric acid with ethylene glycol to provide solution A. Herein, citric acid is used in a molar amount corresponding to 10 times of cerium and ethylene glycol is used in a molar amount corresponding to 40 times of cerium. In the same manner, 213.01 g of citric acid and 252.89 g of ethylene glycol are dissolved at 60° C. for 30 minutes under agitation. Then, 23.56 g of a zirconium (IV) oxychloride octahydrate ($ZrCl_2O \cdot 8H_2O$) as a Zr precursor is dissolved in 30 mL or less of water so that it is dissolved completely therein, and the resultant solution is added gradually to the preformed mixture of citric acid with ethylene glycol to provide solution B. Solution A is mixed with solution B and the mixture is agitated at 60° C. for 30 minutes. Then, the resultant solution is heated at 120 to 130° C. for 5 hours to remove water contained in the solution completely. The obtained sol-like material is maintained at 100° C., 150° C., 200° C. and 300° C., each for 1 hour, at a heating rate of 5° C./min. Then, the material is maintained at 400° C. for 2 hours so that the surface area of the carrier may be maximized. Finally, the material is calcined while maintaining the temperature at 500° C. for 4 hours. Herein, the carrier includes 8 wt % of Ce and 92 wt % of Zr (on the metal basis), and has a specific surface area of 164.5 $m^2/g$.

Then, 0.8 g of the cerium-zirconium oxide carrier obtained as described above in the form of powder is used together with Cu, Zn and Al precursors. As Cu, Zn and Al precursors, 5.51 g of copper acetate hydrate ($Cu(C_2H_3O_2)_2 \cdot H_2O$), 3.03 g of zinc acetate dihydrate ($Zn(C_2H_3O_2)_2 \cdot 2H_2O$), and 2.78 g of aluminum nitrate nonahydrate ($Al(NO_3)_3 \cdot 9H_2O$) are dissolved in 600 mL of deionized water to provide a mixed metal solution having a pH of 5.1. In addition, as a precipitating agent, 5.52 g of sodium carbonate dissolved in 600 mL of deionized water is used, wherein the solution has a pH of 10.2.

In a 2000 mL flask, at 70° C., the mixed metal solution and the precipitating agent solution obtained as described above are added gradually to 200 mL of cerium-zirconium oxide slurried in deionized water at the same time, while maintaining a final pH of 7.5 to 8.0. Herein, the mixed solution is agitated for about 3 hours at 70° C., and the resultant catalyst ($CuZnAl/Ce_{0.08}Zr_{0.92}O_x$) is washed with 2000 mL of deionized water three times or more, filtered, and then dried at 100° C. over at least 12 hours and calcined at 300° C. for 5 hours under air to provide a catalyst for use in methanol synthesis from synthesis gas. The finished catalyst for methanol synthesis has a specific surface area of 123.0 $m^2/g$. The catalyst for methanol synthesis obtained in the form of powder is formed into pellets with a size of 5 mm×2.5 mm, and 320 g of the catalyst is charged into a fixed bed reactor. Then, the catalyst is reduced under hydrogen atmosphere for 4 hours at 250° C. Methanol is synthesized from the synthesis gas obtained from the combined reforming under a pressure of 5.0 MPa with a space velocity of 4300 L/kg cat/h. Herein, the reactor shows a temperature distribution ranging from 241° C. to 290° C.

The catalysts for combined reforming and methanol synthesis are used to carry out an integrated process for preparing methanol from carbon dioxide. The recycle ratio toward the methanol reactor is 0.94 and 6% of unreacted reactants are not recycled to the reactor but discharged to the exterior. The results are shown in the following Tables 4 and 5. After carrying out the integrated process, it is shown that $CO_2$ conversion {((supplied $CO_2$−unconverted $CO_2$)/supplied $CO_2$)×100} is 84%, methanol yield (moles of methanol product/supplied ($CH_4+CO_2$)moles)×100) is about 79%, and methanol production rate is 155 g/h.

TABLE 4

Results of Combined Reforming (Example 1)

| Space velocity (L/kg cat/h) | Molar ratio of reactants (mol %) ($CH_4$/ $H_2O/CO_2$) | Recycle ratio (RR(2)) | Conversion (mol %) $CH_4$ $CO_2$ | Molar ratio of synthesis gas $CO/(CO + CO_2)$ | $H_2/ (2CO + 3CO_2)$ |
|---|---|---|---|---|---|
| 1300 | 1/1.5/0.4 | 0 | 95 46 | 0.83 | 0.91 |

TABLE 5

Results of Methanol Synthesis (Example 1)

| Space velocity (L/kg cat/h) | Molar ratio of reactants CO/ ($CO + CO_2$) | Recycle ratio (RR(1)) | Conversion (mol %) CO $CO_2$ | Methanol production rate (g/h) | Conversion upon recycling (%) |
|---|---|---|---|---|---|
| 4300 | 0.61 | 0.94 | 35 7 | 155 | 84 |

EXAMPLE 2

The integrated process is carried out by using the same catalysts as Example 1, except that the combined reforming is performed under a reaction pressure of 0.65 MPa with a space velocity of 1700 L/kg cat/h by feeding the reactants at a fixed molar ratio of $CH_4:CO_2:H_2O$ of 1:0.39:1.5 to the reforming reactor. In addition, the same catalyst for methanol synthesis as Example 1 is charged to the reactor in an amount of 350 g and the reaction for methanol synthesis is carried out under a reaction pressure of 5.0 MPa with a space velocity of 4700 L/kg cat/h by using the synthesis gas obtained from the combined reforming. Herein, the combined reforming reactor shows a temperature distribution of 755 to 990° C. and the catalyst bed of the reactor for methanol synthesis shows a temperature distribution of 223 to 295° C.

The catalysts for combined reforming and methanol synthesis are used to carry out an integrated process for preparing methanol from carbon dioxide. The recycle ratio toward the methanol reactor is 0.81, the recycle ratio toward the combined reforming reactor is 0.12, and the ratio of unreacted reactants discharged to the exterior is 0.07. The results are shown in the following Tables 6 and 7. After carrying out the integrated process, it is shown that $CO_2$ conversion is 95%, methanol yield is about 80%, and methanol production rate is 202 g/h.

TABLE 6

Results of Combined Reforming (Example 2)

| Space velocity (L/kg cat/h) | Molar ratio of reactants (mol %) ($CH_4$/ $H_2O/CO_2$) | Recycle ratio (RR(2)) | Conversion (mol %) $CH_4$ $CO_2$ | Molar ratio of synthesis gas $CO/(CO + CO_2)$ | $H_2/ (2CO + 3CO_2)$ |
|---|---|---|---|---|---|
| 1700 | 1/1.5/0.39 | 0.12 | 93 57 | 0.87 | 0.93 |

TABLE 7

Results of Methanol Synthesis (Example 2)

| Space velocity (L/kg cat/h) | Molar ratio of reactants CO/ ($CO + CO_2$) | Recycle ratio (RR(1)) | Conversion (mol %) CO $CO_2$ | Methanol production rate (g/h) | Conversion upon recycling (%) |
|---|---|---|---|---|---|
| 4700 | 0.72 | 0.81 | 38 3 | 202 | 67 |

EXAMPLE 3

The integrated process is carried out by using the same catalysts as Example 1, except that the combined reforming is performed under a reaction pressure of 0.55 MPa with a space velocity of 1700 L/kg cat/h by feeding the reactants at a fixed molar ratio of $CH_4:CO_2:H_2O$ of 1:0.34:1.5 to the reforming reactor. In addition, the same catalyst for methanol synthesis as Example 1 is charged to the reactor in an amount of 350 g and the reaction for methanol synthesis is carried out under a reaction pressure of 5.0 MPa with a space velocity of 4300 L/kg cat/h by using the synthesis gas obtained from the combined reforming. Herein, the combined reforming reactor shows a temperature distribution of 755 to 995° C. and the catalyst bed of the reactor for methanol synthesis shows a temperature distribution of 216 to 298° C.

The catalysts for combined reforming and methanol synthesis are used to carry out an integrated process for preparing methanol from carbon dioxide. The recycle ratio toward the methanol reactor is 0.90, the recycle ratio toward the combined reforming reactor is 0.08, and the ratio of unreacted reactants discharged to the exterior is 0.02. The results are shown in the following Tables 8 and 9. After carrying out the integrated process, it is shown that $CO_2$ conversion is 95%, methanol yield is about 95%, and methanol production rate is 215 g/h.

TABLE 8

Results of Combined Reforming (Example 3)

| Space velocity (L/kg cat/h) | Molar ratio of reactants (mol %) ($CH_4$/$H_2O$/$CO_2$) | Recycle ratio (RR(2)) | Conversion (mol %) $CH_4$ | Conversion (mol %) $CO_2$ | Molar ratio of synthesis gas CO/(CO + $CO_2$) | Molar ratio of synthesis gas $H_2$/(2CO + 3$CO_2$) |
|---|---|---|---|---|---|---|
| 1700 | 1/1.5/0.34 | 0.08 | 97 | 44 | 0.84 | 1.02 |

TABLE 9

Results of Methanol Synthesis (Example 3)

| Space velocity (L/kg cat/h) | Molar ratio of reactants CO/(CO + $CO_2$) | Recycle ratio (RR(1)) | Conversion (mol %) CO | Conversion (mol %) $CO_2$ | Methanol production rate (g/h) | Conversion upon recycling (%) |
|---|---|---|---|---|---|---|
| 4300 | 0.68 | 0.90 | 53 | 8 | 215 | 87 |

EXAMPLE 4

To determine the composition in each unit process represented by the flow chart of FIG. 2 through modeling using the results of Example 3, ASPEN PLUS is used to simulate the process, and the results are shown in the following Table 10. To perform the simulation, it is assumed that the recycle ratios toward the reactor for methanol synthesis and toward the combined reforming reactor are fixed at 0.8 and 0.19, respectively, and the flow ratio of unreacted reactants discharged to the exterior is 0.01. The results are summarized in Table 10. Herein, stream 10 in FIG. 3, which is passed through the combined reforming reactor, combined with unreacted reactants and then fed into the reactor for methanol synthesis, has a $H_2/(2CO+3CO_2)$ ratio of 1.22. Such a ratio is slightly away from the range suitable for methanol synthesis. It is thought that this results from a decrease in recycle ratio toward the reactor for methanol synthesis to 0.8 or less.

TABLE 10

| Stream # | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|
| Mole Flow (kmol/h) | 1.00 | 1.50 | 0.34 | 6.66 | 5.90 | 0.81 | 7.49 | 13.39 | 10.70 | 9.32 | 1.38 | 0.05 | 1.78 | 1.33 | 1.26 | 0.07 |
| Mole % | | | | | | | | | | | | | | | | |
| $CH_4$ | 100 | 0.00 | 0.00 | 0.36 | 0.41 | 0.00 | 1.24 | 0.87 | 1.08 | 1.23 | 0.07 | 2.08 | 1.24 | 0.00 | 0.00 | 0.00 |
| $H_2O$ | 0.00 | 100 | 0.00 | 11.45 | 0.27 | 94.20 | 0.01 | 0.01 | 0.58 | 0.01 | 4.49 | 0.00 | 0.01 | 4.65 | 0.00 | 89.86 |
| CO | 0.00 | 0.00 | 0.00 | 22.37 | 25.24 | 0.00 | 12.81 | 18.39 | 11.21 | 12.86 | 0.07 | 2.08 | 12.81 | 0.00 | 0.00 | 0.00 |
| $H_2$ | 0.00 | 0.00 | 0.00 | 61.21 | 69.08 | 0.00 | 75.13 | 72.96 | 65.78 | 75.49 | 0.14 | 4.17 | 75.13 | 0.00 | 0.00 | 0.00 |
| $CO_2$ | 0.00 | 0.00 | 100 | 4.34 | 4.90 | 0.12 | 10.22 | 7.70 | 9.01 | 9.88 | 3.12 | 75.00 | 10.22 | 0.53 | 0.00 | 10.14 |
| $CH_3OH$ | 0.00 | 0.00 | 0.00 | 0.27 | 0.10 | 5.68 | 0.60 | 0.08 | 12.34 | 0.52 | 92.10 | 16.67 | 0.60 | 94.82 | 100 | 0.00 |

In a variant, to perform the simulation, it is assumed that the recycle ratios toward the reactor for methanol synthesis and toward the combined reforming reactor are fixed at 0.90 and 0.09, respectively, and the flow ratio of unreacted reactants discharged to the exterior is 0.01. The results are summarized in Table 11. Herein, stream 10 in FIG. 3, which is passed through the combined reforming reactor, combined with unreacted reactants and then fed into the reactor for methanol synthesis, has a $H_2/(2CO+3CO_2)$ ratio of 0.95. Such a ratio is within the range suitable for methanol synthesis.

TABLE 11

| Stream # | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|
| Mole Flow (kmol/hr) | 1.00 | 1.50 | 0.34 | 5.66 | 4.93 | 0.78 | 7.70 | 12.63 | 9.91 | 8.49 | 1.42 | 0.07 | 0.77 | 1.35 | 1.26 | 0.09 |
| Mole % | | | | | | | | | | | | | | | | |
| $CH_4$ | 100 | 0.00 | 0.00 | 0.44 | 0.51 | 0.00 | 2.72 | 16 | 2.35 | 2.73 | 0.07 | 1.43 | 2.72 | 0.00 | 0.00 | 0.00 |
| $H_2O$ | 0.00 | 100 | 0.00 | 13.03 | 0.28 | 94.99 | 0.01 | 0.01 | 0.84 | 0.01 | 5.86 | 0.00 | 0.01 | 6.09 | 0.00 | 91.11 |
| CO | 0.00 | 0.00 | 0.00 | 23.67 | 27.16 | 0.00 | 13.70 | 19.13 | 11.84 | 13.80 | 0.07 | 1.43 | 13.70 | 0.00 | 0.00 | 0.00 |
| $H_2$ | 0.00 | 0.00 | 0.00 | 57.97 | 66.53 | 0.00 | 67.85 | 67.91 | 58.63 | 68.39 | 0.14 | 2.86 | 67.85 | 0.00 | 0.00 | 0.00 |
| $CO_2$ | 0.00 | 0.00 | 100 | 4.77 | 5.47 | 0.13 | 15.06 | 11.02 | 13.08 | 14.53 | 4.38 | 78.57 | 15.06 | 0.59 | 0.00 | 8.89 |
| $CH_3OH$ | 0.00 | 0.00 | 0.00 | 0.12 | 0.04 | 4.88 | 0.65 | 0.07 | 13.26 | 0.53 | 89.48 | 15.71 | 0.65 | 93.32 | 100 | 0.00 |

As can be seen from the foregoing, in the highly efficient process for preparing methanol using carbon dioxide, it is necessary to maintain the molar ratio of reactants for combined reforming ($CH_4/CO_2/H_2O$) at 1/0.3-0.6/1.0-2.0 in order to maintain a predetermined molar ratio of synthesis gas of carbon monoxide, carbon dioxide and hydrogen ($H_2/(2CO+3CO_2)$=0.85-1.15) as the products of combined reforming. In addition to this, it is required to control the recycle ratios toward the reactor for methanol synthesis and toward the combined reforming reactor within an adequate range. Particularly, when the ratio of synthesis gas in the unreacted reactants remaining after methanol synthesis and recycled toward combined reforming is maintained at 0.0 to 0.2, and the ratio of the unreacted synthesis gas recycled toward methanol synthesis is maintained at 0.8 to 1.0, it is possible to obtain the ratio of synthesis gas suitable for methanol synthesis ($H_2/(2CO+3CO_2)$=0.85-1.15). In conclusion, it is possible to maximize carbon availability (methane and $CO_2$ availability) and energy efficiency by using the catalyst systems according to our previous studies and by selecting an adequate recycle ratio of unreacted materials.

INDUSTRIAL APPLICABILITY

In 2005, as a measure to deal with global warming, the Kyoto protocol regarding reduction of carbon dioxide emission is enacted. Under these circumstances, it is getting important gradually to develop technologies of reducing carbon dioxide emission and producing energy-containing materials from carbon dioxide. The present disclosure provides an integrated process including carrying out combined reforming of carbon dioxide reforming of methane and steam reforming of methane as a process for economical utilization of carbon dioxide to produce synthesis gas, and synthesizing methanol from the obtained synthesis gas. In this manner, it is possible to maximize energy efficiency and carbon availability. The primary product, methanol, is useful as a starting material for producing various industrial products, such as DME, DMC, biodiesel and synthetic gasoline. Further, the synthesis gas obtained from the combined reforming is useful for Fischer-Tropsch synthesis. Therefore, the method disclosed herein is expected to contribute to development of processes for economical utilization of carbon dioxide.

The invention claimed is:

1. A method for preparing methanol from carbon dioxide, comprising:

preparing synthesis gas having $H_2/(2CO+3CO_2)$ mole ratio of 0.85~1.15 via combined reforming, in which steam reforming of natural gas is carried out simultaneously with carbon dioxide reforming of methane, in the presence of a catalyst of $Ni/Ce/MgAlO_x$ or $Ni/Ce-Zr/MgAlO_x$, wherein said preparing synthesis gas is performed by carrying out combined reforming at a reaction temperature of 800 to 1,000° C. under a reaction pressure of 05~20 atm with a space velocity of 1,000 to 500,000 $h^{-1}$ in such a condition that molar ratio of $CH_4/CO_2/H_2O$ is within a range of 1/0.3-0.6/1.0-2.0;

synthesizing methanol from the obtained synthesis gas in the presence of a catalyst of $Cu-ZnO-Al_2O_3/CeZrOx$; and separating the methanol product from unreacted synthesis gas and recycling 10 the unreacted synthesis gas.

2. The method for preparing methanol from carbon dioxide according to claim 1, wherein the unreacted synthesis gas separated from the methanol product is recycled to said preparing synthesis gas or said synthesizing methanol.

3. The method for preparing methanol from carbon dioxide according to claim 1, wherein said synthesizing methanol is carried out at a reaction temperature of 200 to 400° C. under a reaction pressure of 30 to 60 kg/cm² with a space velocity of 1,000 to 10,000 $^{-1}$.

4. The method for preparing methanol from carbon dioxide according to claim 2, wherein the unreacted synthesis gas separated from the methanol product is recycled in such a manner that the ratio of synthesis gas recycled to combined reforming is maintained at 0.0 to 0.2 and that of synthesis gas recycled to methanol synthesis is maintained at 0.8 to 1.0, based on the total unreacted reactants.

5. The method for preparing methanol from carbon dioxide according to claim 1, wherein said preparing synthesis gas provides a methane conversion of 90% or higher and a carbon dioxide conversion of 40% or higher.

6. The method for preparing methanol from carbon dioxide according to claim 1, wherein said synthesizing methanol provides a CO conversion of 35% or higher.

* * * * *